US009404362B2

(12) United States Patent
Jung et al.

(10) Patent No.: US 9,404,362 B2
(45) Date of Patent: Aug. 2, 2016

(54) MATERIAL CHARACTERISTIC ESTIMATION USING INTERNAL REFLECTANCE SPECTROSCOPY

(71) Applicants: Sebastian Jung, Isernhagen (DE); Felix Wellmann, Ronnenberg (DE); Thomas Kruspe, Wietzendorf (DE)

(72) Inventors: Sebastian Jung, Isernhagen (DE); Felix Wellmann, Ronnenberg (DE); Thomas Kruspe, Wietzendorf (DE)

(73) Assignee: BAKER HUGHES INCORPORATED, Houston, TX (US)

( * ) Notice: Subject to any disclaimer, the term of this patent is extended or adjusted under 35 U.S.C. 154(b) by 5 days.

(21) Appl. No.: 14/091,752

(22) Filed: Nov. 27, 2013

(65) Prior Publication Data
US 2015/0144776 A1 May 28, 2015

(51) Int. Cl.
*G01V 5/08* (2006.01)
*E21B 49/08* (2006.01)
*G01N 21/552* (2014.01)

(52) U.S. Cl.
CPC ............ *E21B 49/087* (2013.01); *G01N 21/552* (2013.01); *E21B 2049/085* (2013.01)

(58) Field of Classification Search
CPC ......... G01J 3/42; G01N 21/031; G01N 21/31; G01N 21/552; G01N 30/74
See application file for complete search history.

(56) References Cited

U.S. PATENT DOCUMENTS

| 4,883,956 | A |   | 11/1989 | Melcher et al. |
|---|---|---|---|---|
| 5,051,551 | A |   | 9/1991 | Doyle |
| 5,167,149 | A |   | 12/1992 | Mullins et al. |
| 5,835,231 | A | * | 11/1998 | Pipino ............................ 356/440 |
| 6,388,251 | B1 |   | 5/2002 | Papanyan |
| 7,095,012 | B2 | * | 8/2006 | Fujisawa et al. ........... 250/269.1 |
| 2003/0138067 | A1 |   | 7/2003 | Tiller et al. |
| 2005/0211433 | A1 |   | 9/2005 | Wilson et al. |
| 2007/0284518 | A1 |   | 12/2007 | Randall |
| 2010/0224773 | A1 |   | 9/2010 | Galford et al. |

FOREIGN PATENT DOCUMENTS

| EP | 07047569 A2 | 12/1996 |
|---|---|---|
| WO | 9900575 A2 | 1/1999 |

OTHER PUBLICATIONS

Mullins, et al., "Downhole Determination of GOR on Single-Phase Fluids by Optical Spectroscopy", SPWLA 42nd Annual Logging Symposium, Jun. 17-20, 2001, pp. 1-14.

(Continued)

*Primary Examiner* — Kiho Kim
(74) *Attorney, Agent, or Firm* — Cantor Colburn LLP

(57) ABSTRACT

An apparatus for measuring fluid characteristics includes: a solid transparent body including a plurality of internally reflective surfaces defining a n-sided base having a polygonal shape and having at least three sides, each reflective surface forming a side of the polygonal shape, the plurality of surfaces configured to direct the electromagnetic radiation beam along a path within the solid transparent body from an entry area to an exit area on the solid transparent body; an electromagnetic radiation source coupled to the entry area on the solid transparent body; and a detector coupled to the exit area on the solid transparent body and configured to receive at least a fraction of the reflected electromagnetic radiation beam, the detector configured to generate a signal based on the received electromagnetic radiation beam and transmit the signal to a processor for at least one of analysis of material characteristics and data storage.

19 Claims, 6 Drawing Sheets

(56) References Cited

OTHER PUBLICATIONS

Notification of Transmittal of the International Search Report and the Written Opinion of the International Searching Authority, or the Declaration; PCT/US2014-066837; Mailed Feb. 24, 2015, 13 pages.

O'Leary, "Attenuated Total Reflection Spectroscopy method for measuring dissolved Co2 concentration in Beer", VitalSensors Technologies, LLC, 2005, 4 pages.

Ramesh et al., "Techniques in exploration and Formation Evaluation for Gas Hydrates", 7th International Conference & Exposition on Petroleum Geophysics, 2008, 6 pages.

* cited by examiner

MATERIAL CHARACTERISTIC ESTIMATION USING INTERNAL REFLECTANCE SPECTROSCOPY

BACKGROUND

In energy industries, fluid testing is an important component in evaluation of formations and oil and gas production. Such testing can be useful in evaluating the hydrocarbon content of a formation or drilling fluid, and can be performed downhole, e.g., during drilling. Internal reflectance spectroscopy is a process that is useful for evaluating formation fluids. Internal reflectance spectroscopy utilizes a transparent crystal having a surface in contact with a fluid. Internal reflections of a light beam inside the crystal from the crystal-fluid interface are evaluated to estimate fluid properties.

SUMMARY

An apparatus for measuring fluid characteristics includes: a solid transparent body including a plurality of internally reflective surfaces configured to contact a material of interest and configured to internally reflect an electromagnetic radiation beam, the plurality of reflective surfaces defining a n-sided base having a polygonal shape and having at least three sides, each reflective surface forming a side of the polygonal shape, the plurality of surfaces configured to direct the electromagnetic radiation beam along a path within the solid transparent body from an entry area to an exit area on the solid transparent body; an electromagnetic radiation source coupled to the entry area on the solid transparent body and configured to transmit the electromagnetic radiation beam into the solid transparent body through the entry area; and a detector coupled to the exit area on the solid transparent body and configured to receive at least a fraction of the reflected electromagnetic radiation beam, the detector configured to generate a signal based on the received electromagnetic radiation beam and transmit the signal to a processor for at least one of analysis of material characteristics and data storage.

A method of measuring fluid characteristics includes: generating an electromagnetic radiation beam by a source coupled to an entry area on an internal reflectance solid transparent body; transmitting the electromagnetic radiation beam into the solid transparent body through the entry area; guiding the electromagnetic radiation beam along a path through the solid transparent body to an exit area on the solid transparent body, wherein guiding includes totally internally reflecting the electromagnetic radiation beam from each of a plurality of internally reflective surfaces of the solid transparent body in contact with a material of interest, the plurality of reflective surfaces defining a n-sided base having a polygonal shape and having at least three sides, each reflective surface forming a side of the polygonal shape; receiving the electromagnetic radiation beam from the exit area at a detector; and analyzing characteristics of the material of interest based on the received electromagnetic radiation beam.

DETAILED DESCRIPTION

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

DETAILED DESCRIPTION

Apparatuses and methods for performing parameter measurements using reflectance spectroscopy are described. An embodiment of a reflectance spectroscopy measurement assembly, such as an attenuated total reflectance (ATR) spectroscopy assembly, includes an internal reflectance crystal or other solid transparent body configured to contact a material of interest.

An embodiment of an internal reflectance crystal or other solid transparent body includes a plurality of internally reflective surfaces configured to be disposed in contact with a fluid or other material of interest, i.e., a material to be measured. The body is made from a transparent material having a higher refractive index than the refractive index of the material of interest. The reflective surfaces form a polygonal shape and guide an interrogation beam from an input area on the body to an output area on the body. The solid transparent body is shaped to provide a large number of reflections while maintaining a small size sufficient for use in downhole applications.

An exemplary spectroscopy method includes transmitting a light beam (e.g., a mid-infrared light beam) or other electromagnetic radiation into a crystal or other solid transparent body having a plurality of reflective surfaces in contact with a material of interest, internally reflecting the light beam from the plurality of reflective surfaces, and detecting the reflected light beam. The reflected light beam is analyzed to estimate characteristics of the material. For example, spectroscopy is performed on borehole fluids and/or formation fluids to detect characteristics of such fluids, such as the presence of methane or other hydrocarbons. The method can be performed as a wireline method or during drilling, and can be performed in real time.

Figure 1:
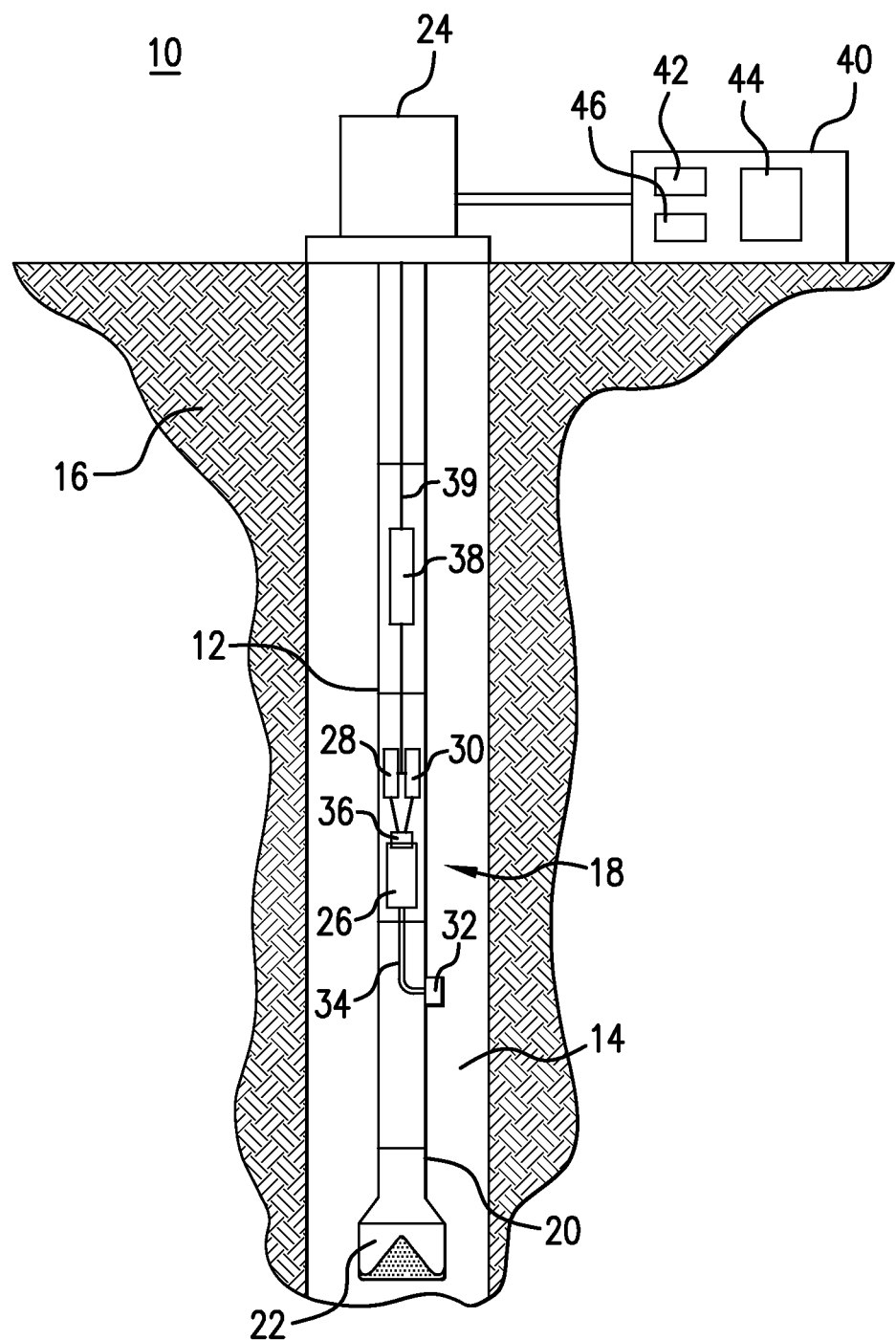
FIG. 1 is a side cross-sectional view of an embodiment of a subterranean well drilling, evaluation, exploration and/or production system.

Referring to FIG. 1, an exemplary embodiment of a subterranean well drilling, measurement, exploration and/or production system 10 includes a borehole string 12 that is shown disposed in a borehole 14 that penetrates at least one earth formation 16 during a subterranean operation. The borehole 14 may be an open or cased borehole. In one embodiment, the borehole string includes a downhole tool 18 such as a well logging and/or sampling tool. The downhole tool 18 may be a wireline tool or may be incorporated with a drill string in, e.g., a bottomhole assembly (BHA) for use in drilling and/or logging-while-drilling (LWD) applications. The system 10 and/or the borehole string 12 include any number of downhole tools 18 for various processes including drilling, hydrocarbon production, and measurement of one or more physical quantities in or around a borehole.

The downhole tool 18 is not limited to the embodiments described herein, and may be disposed with any suitable carrier. A "carrier" as described herein means any device, device component, combination of devices, media and/or member that may be used to convey, house, support or otherwise facilitate the use of another device, device component, combination of devices, media and/or member. Exemplary non-limiting carriers include drill strings of the coiled tube type, of the jointed pipe type and any combination or portion thereof. Other carrier examples include casing pipes, wirelines, wireline sondes, slickline sondes, drop shots, downhole subs, bottom-hole assemblies, and drill strings.

In one embodiment, the system 10 is configured as a downhole drilling system 10 that includes a drill string 12 disposed in the borehole 14. Although the borehole 14 is shown in FIG. 1 to be vertical and of constant diameter, the borehole 14 is not so limited. For example, the borehole 14 may be of varying diameter and/or direction (e.g., azimuth and inclination). The drill string 12 is made from, for example, a pipe or multiple pipe sections.

The system 10 and/or the drill string 12 include a drilling assembly 20, which may be configured as a bottomhole assembly (BHA). The drilling assembly 20 includes a drill bit 22 that is attached to the bottom end of the drill string 12 via various drilling assembly components. The drilling assembly 20 is configured to be conveyed into the borehole 14 from a drilling rig 24.

The downhole tool 18, in one embodiment, is a sampling and/or measurement tool or assembly that performs measurements of downhole fluids using internal reflectance spectroscopy. An example of internal reflectance spectroscopy is attenuated total reflectance (ATR) spectroscopy. For an internal reflectance spectroscopy process, an internal reflectance body such as an internal reflectance crystal is configured to be in contact with a fluid sample or other material of interest. An electromagnetic radiation or light source transmits light to the crystal, undergoes total internal reflection at the crystal faces, and returns to a spectrometer. The return signal is analyzed to determine characteristics such as chemical composition of the fluid sample. As described herein, a "sample" refers to any amount or volume of a material of interest, i.e., a material for which characteristics are to be measured. Such material may be a fluid material, a solid material or a combination.

In one embodiment, the material is a downhole material taken from an earth formation. Exemplary materials include fluids that may be present in the formation and/or borehole, such as drilling fluid, borehole fluids, formation fluids and combinations thereof.

A material sample can be analyzed in any suitable manner that contacts the solid transparent body to a volume of the fluid, e.g., by extracting a fluid sample to a sample chamber in the tool 18 or borehole string 12, by extracting a fluid sample to the surface, by directly exposing the body to fluid circulating in the borehole, or by contacting fluid in the formation (e.g., using a coring tool or drill bit to allow a probe to extend into the formation).

An exemplary measurement tool 18 shown in FIG. 1 includes a sampling module configured to retrieve a fluid sample, a sample storage chamber 26, a light source assembly 28, a detector assembly 30 and one or more processing or electronics assemblies. The sampling module includes a sampling probe 32 coupled to the storage chamber 26 by a flow line 34. The sampling probe 32 can have any suitable configuration for retrieving a fluid sample. For example, the sampling probe 32 can include an extendable or stationary port for admitting borehole fluids. In another example, the sampling probe 32 includes or is used in conjunction with a coring bit or other mechanism for penetrating the formation and extracting fluids.

The light source assembly 28 is optically coupled to an internal reflectance crystal 36, a portion of which is submerged in or otherwise in contact with the fluid sample in the storage chamber 26. It is noted that embodiments herein are not limited to including a storage chamber. Any configuration that causes the crystal to contact fluid or other material of interest may be used. Light reflected in the crystal 36 is transmitted to the detector assembly 30. Although embodiments described herein include a light beam, light signal or light source, they are not so limited. It is understood that light beams, signals and sources can include any suitable electromagnetic radiation, which includes radiation having wavelengths in the visible and non-visible spectrums.

The light source assembly 28 and/or the detector assembly 30 are connected to suitable processing and electronics components to control the light source and associated components, receive data from detectors, transmit data, store data and/or analyze data for estimation of fluid characteristics. For example, downhole electronics 38 are disposed in the tool 18 or otherwise in the borehole string for storing, transmitting and/or processing signals and/or data generated by the tool 18. In one embodiment, the tool 18 is equipped with transmission equipment such as a communication cable 39 to communicate ultimately to a surface processing unit 40. Such transmission equipment may take any desired form, and different transmission media and methods may be used. Examples of connections that can be used for transmission include wired, fiber optic, wireless connections and memory based systems or mud pulse telemetry.

The processing unit 40 is connected in operable communication with the tool 18, the drilling assembly 20 and/or other downhole components. The processing unit 40 may be located, for example, at a surface location, a subsea location and/or a surface location on a marine well platform or a marine craft. The processing unit 40 may also be incorporated with the drill string, the measurement tool and/or the drilling assembly, or otherwise disposed downhole as desired. The processing unit 40 may be configured to perform functions such as controlling the measurement tool 18 and/or the drilling assembly 20, transmitting and receiving data, monitoring and analysis of measurement data. The processing unit 40, in one embodiment, includes a processor 42, a data storage device (or a computer-readable medium) 44 for storing, data, models and/or computer programs or software 46.

Figure 2:
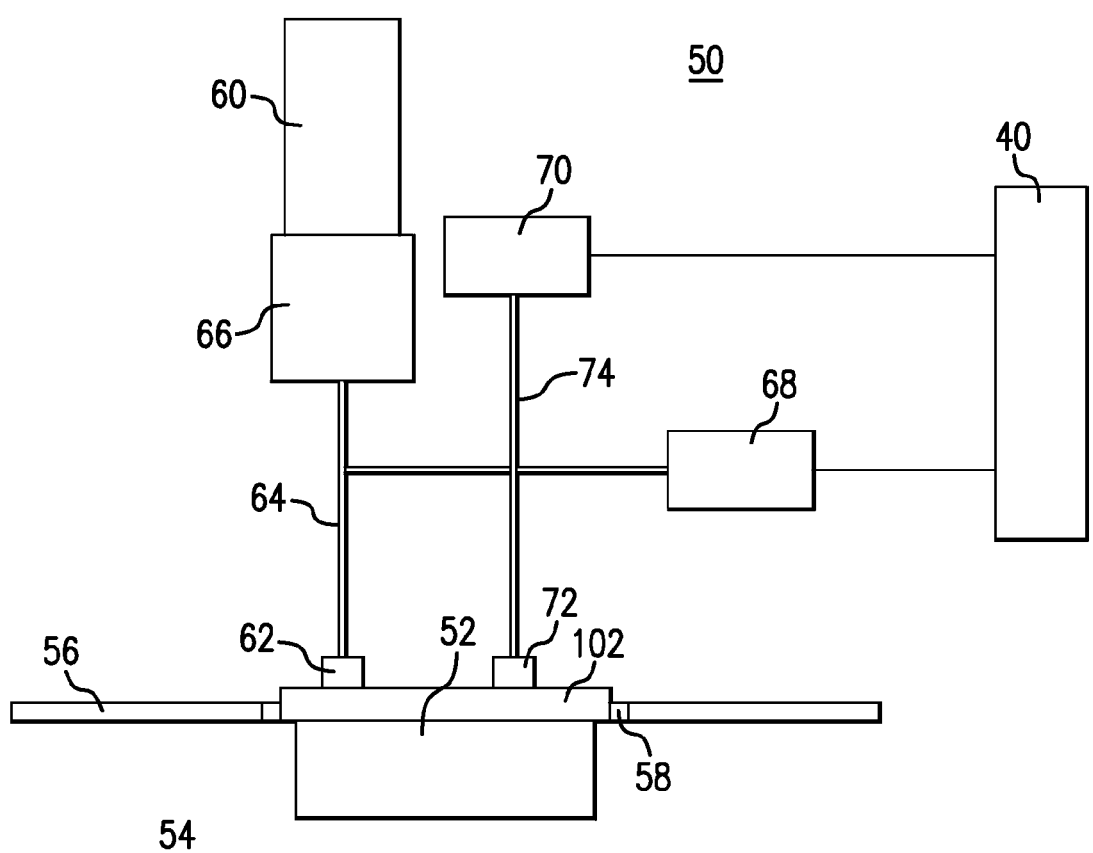
FIG. 2 is a side cross-sectional view of an embodiment of a reflectance spectroscopy measurement assembly.

FIG. 2 illustrates an exemplary measurement assembly 50 that is part of a measurement device such as the tool 18. The measurement assembly includes a solid transparent body such as an internal reflectance crystal 52 that is coupled to a fluid sample 54 disposed in, e.g., a sample chamber 56. A portion of the crystal 52, including surfaces of the crystal at which a light signal is to be reflected, is submerged in the fluid sample. The crystal 52 includes or is coupled to a sealing mechanism such as an O-ring 58 to isolate the fluid sample from other components of the measurement assembly 50.

Although embodiments described herein include a crystal, they are not so limited. Any solid body that is transparent at least to the wavelengths of light signals used for measurement (e.g., glass bodies) may be used. Accordingly, it is understood that any description of a crystal herein contemplates any suitable transparent body.

The measurement assembly 50 includes a light source 60, such as a tunable light source, a black-body source or a gray-body source in combination with a tunable or non-tunable/static optical filter, that is optically coupled to a selected entry area of the crystal 52 via a suitable optical assembly 62 and an input optical fiber 64. An exemplary light source 60 is a broad band light source coupled to a tuning device 66 such as an acousto-optical tunable filter (AOTF) that transmits light of a single frequency to the input fiber 64. A reference detector 68 may be included to measure the input signal. An output signal detector 70 is coupled to an exit area of the crystal 62 via, e.g., an optical assembly 72 and an output optical fiber 74. The source and detectors are communicatively coupled to a processor such as the surface processing unit 40. The entry area and the exit area may be at the same location on a surface of the crystal 52 or be at different locations.

The sealing mechanism is not limited to the embodiments described herein. Any suitable sealing mechanism may be used. For example, the assembly 50 could be configured so that an O-ring or other seal is located near the entry area and/or the exit area.

The processor may scan a predefined spectral interval or obtain data at a number of selected frequencies, control the light source 60 to emit light at selected frequencies or control the filter or other wiring device 66 to emit light at selected frequencies (e.g., from about 1500-1520 nm, from about 1520-1540 nm, etc.), and receive a signal indicative of the energy in the light at the selected frequencies as a reference. Light is passed into the crystal 52 by the optical assembly 62 or other connector or coupler. This light undergoes total internal reflection at the faces of the crystal that are in contact with the formation fluid. The reflected light passes through the exit area to the optic fiber 74 and thence to the detector 70, which sends a signal to the processor that is indicative of the energy in the reflected light.

In total reflectance spectrometry, such as ATR spectrometry, a beam of light hits at least one surface at which total reflection can occur. The surface is in contact with a material of interest, which has an index of refraction that is lower than the crystal's index of refraction. If the material is a medium in which an electromagnetic wave can propagate, a so-called evanescent wave accrues and penetrates into the material.

Figure 3:
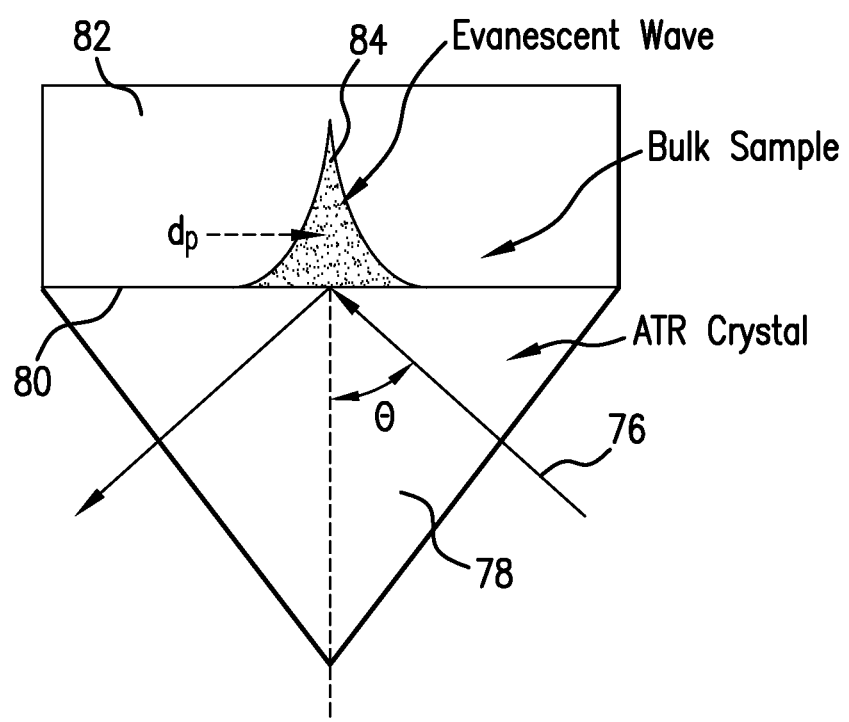
FIG. 3 is an illustration of an internal reflectance solid transparent body in contact with a sample to be measured.

For example, as shown in FIG. 3, a light beam 76 is transmitted into the interior of an internal reflection crystal 78. The beam 76 is internally reflected from a surface 80 of the crystal 78, which is in contact with a material to be measured, shown in FIG. 3 as a bulk sample 82. Reflection forms an evanescent wave 84 that penetrates into the bulk sample 82. The penetration depth $d_p$ of the evanescent wave is determined by the wavelength of the beam, the angle of incidence $\theta$, and the indexes of refraction of the crystal and the bulk sample medium. If the penetrated medium absorbs light at this wavelength, the evanescent wave will be partially absorbed, otherwise it will be totally reflected on the contact surface between the optically different materials (materials having different indexes of refraction). By changing the wavelength, the absorbance spectra of the sample can be determined.

In some cases it is necessary to have multiple reflections on which total reflection occurs. The first reason is a very low absorption caused by the fluid properties. The second reason is a very low absorption due to a very low molar concentration. In these cases it is important to have multiple reflections to generate a sufficient signal-to-noise ratio and allow changes in light intensity to be measured.

Figure 4:
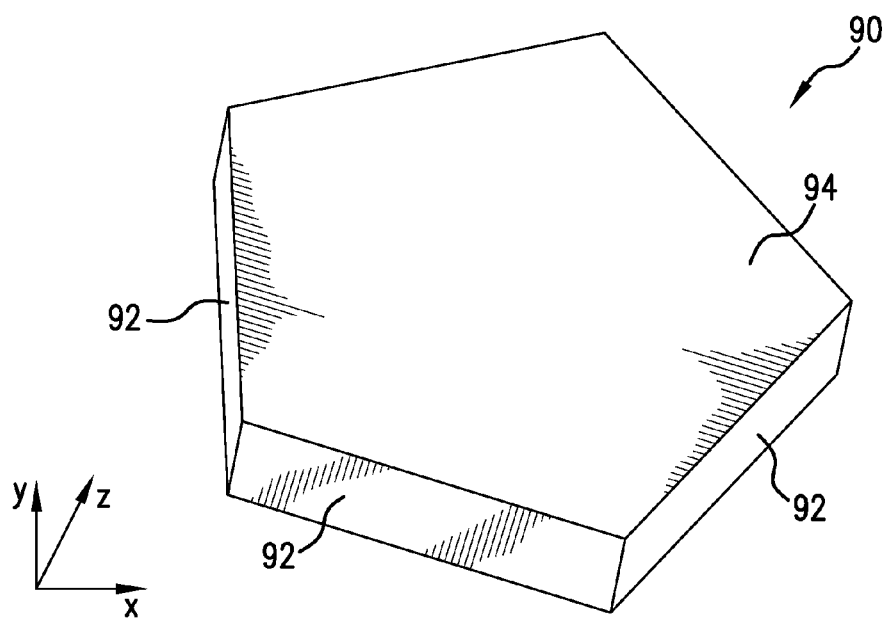
FIG. 4 is a perspective view of an embodiment of an internal reflectance solid transparent body for use in a reflectance spectroscopy measurement assembly.

FIG. 4 shows an embodiment of a multiple reflection, internal reflection body such as a crystal 90 configured for use in an internal reflectance spectroscopy system or device, such as an ATR spectrometry device. The crystal has a shape that provides multiple reflective surfaces formed by the exterior of the crystal. A plurality of the reflective surfaces are each capable of being submerged or otherwise disposed in contact with a fluid or other material of interest. An optical beam transmitted into the crystal is directed such that the beam propagating through the interior of the crystal is entirely reflected by each surface and results in an evanescent wave in the fluid sample near the surface. The crystal is made of a material that is transparent to selected wavelengths corresponding to wavelengths of interrogation signals transmitted into the crystal. For example, if infrared spectroscopy signals are transmitted, the crystal is made from sapphire or another material transparent to the infrared wavelengths of the interrogation signals.

An optical beam is transmitted into the crystal so that the beam propagates within the crystal material and contacts each surface in contact with the material of interest at an angle that is larger with respect to the normal to the surface than the critical angle determined by the refractive indexes of the crystal and the material of interest. In this way, each of the surfaces totally internally reflects the beam and, as discussed above, causes an evanescent wave in the material of interest.

In one embodiment, each of a plurality of the internally reflective surfaces defines a polygon prism or polygonal shape having at least three sides. A "polygonal shape", in one embodiment, refers to the shape of a plane or base formed by the connection of at least some of the plurality of reflective surfaces. For example, as shown in FIG. 4, the upper and/or lower edges of a plurality of reflective surfaces 92 connect to form a polygonal base. Each side of the polygon is formed by one of the reflective surfaces. In one embodiment, the number and position of the reflective surfaces are selected such that the optical beam paths, which are straight paths between consecutive reflections, form a chain of straight line segments having an overall beam path that is generally circular, ring-shaped or elliptical. The number and position of surfaces are selected to control the beam path and the number of reflections that occur in the crystal before the beam exits the crystal.

The crystal has both a relatively small size such that the crystal can be incorporated with a downhole spectrometer, and provides a sufficient number of reflections such that a sufficient light intensity change can be measured with an acceptable signal-to-noise ratio.

An embodiment of the crystal is shown in FIG. 4. A crystal 90 includes a number of internally reflective surfaces 92 that form a polygonal base shape. Each reflective surface 92 forms a side of a polygon. In the embodiment shown in FIG. 4, the reflective surfaces 92 form a pentagon, although other shapes may be employed. For example, the base shape may be similar to a pentagon, hexagon, heptagon, etc.

In one embodiment, the polygonal shape forms a regular polygon, in which the length of each reflective surface 92 forming a side is equal and each reflective surface 92 forms the same angle to each of the adjoining sides. In one embodiment, each reflective surface 92 also has the same surface area.

In the embodiment shown in FIG. 4, the reflective surfaces 92 form a polygon in a plane (shown in this example as the x-y plane) that is perpendicular to the reflective surfaces 92 (which extend in the z-direction in this example). Reflections may also occur on the top and bottom surfaces of the polygonal prism. In other embodiments, the surfaces 92 may be partially perpendicular to the plane, i.e., oriented at an angle less than 90 degrees relative to the plane. The crystal 90 includes a top surface 94 that extends in the x-y plane. In one embodiment, the reflective surfaces 92 and the top surface 94 are disposed in contact with the sample when spectroscopy is performed. The crystal 90 may also have a bottom surface extending in the x-y plane.

Figure 5:
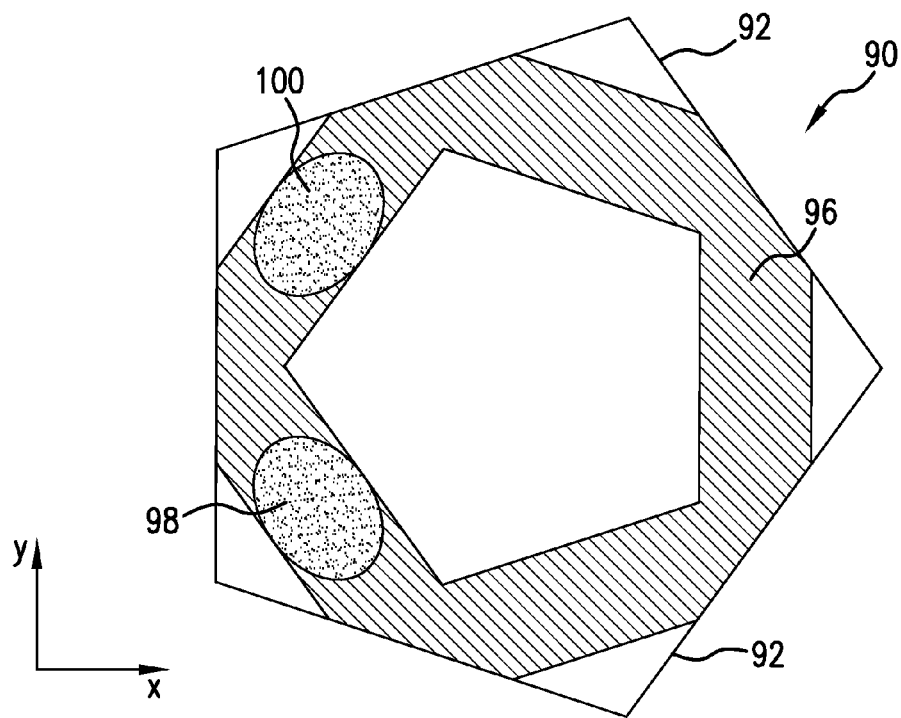
FIG. 5 is a top view of an embodiment of an internal reflectance solid transparent body and an exemplary path of an interrogation signal in the solid transparent body.

FIG. 5 shows a top view of a ray path 96 of an input light beam that is coupled to the crystal 90 and reflects from the reflective surfaces 92 and may also reflect from the top surface 94 and/or the bottom surface. In the embodiment shown in FIG. 5, the reflective surfaces 92 and the top surface 94 are in contact with the sample. Only the total reflections on the side areas are in view in FIG. 5. Also shown is an exemplary entry location or area 98 and an exit location or area 100 at which the beam enters and exits the crystal 90 respectively. The entry area 98 and the exit area 100, in one embodiment, are not the same and do not overlap each other. The entry and exit areas are shown in this embodiment as both being on the bottom surface, but are not so limited. Input and output areas can be disposed on a top and/or bottom surface, and can also be disposed on a side surface such as one of the surfaces 92. It is noted that the size, shape and number of reflective surfaces is not limited to this example, and that crystals or transparent bodies having different numbers of surfaces and different sizes may be used.

Figure 6:
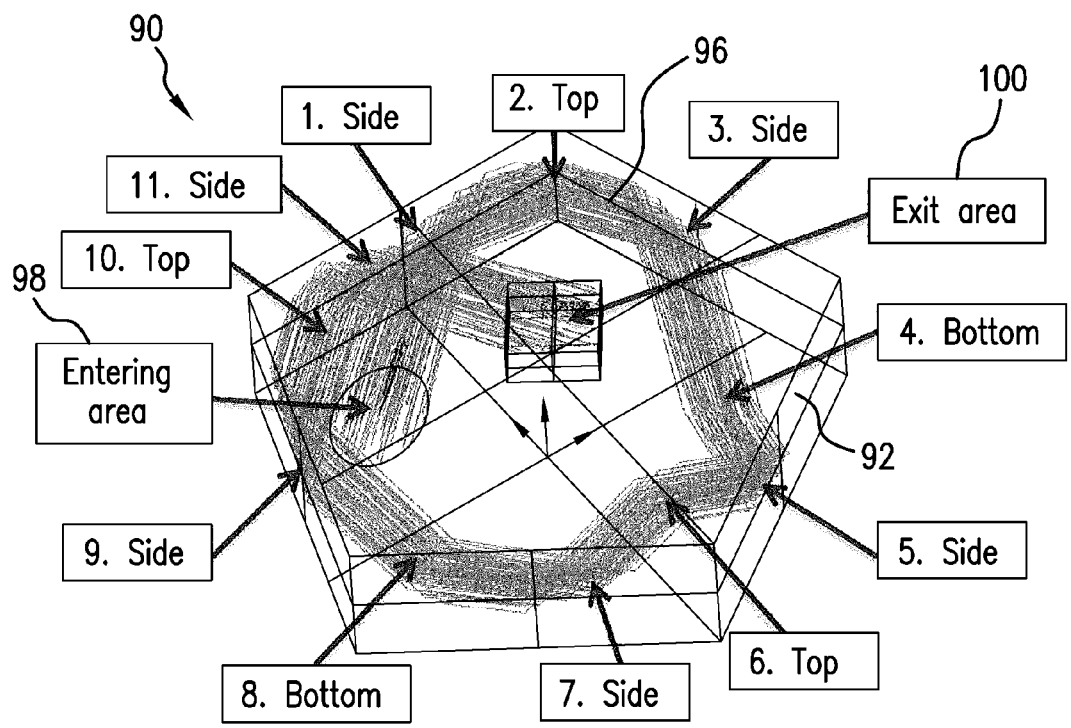
FIG. 6 is a perspective view of an embodiment of an internal reflectance solid transparent body and an exemplary path of an interrogation signal in the solid transparent body.

Another embodiment of the crystal 90 is shown in FIG. 6. In this embodiment, all side areas and the top area are in contact with the sample, and both the entry and exit areas are disposed on the bottom surface. As shown, a beam entering the crystal 90, so that the angles of incidence are larger than the critical angle with respect to the normal to the surface for each surface 92, reflects from each side surface 92 and can also reflect from the top and bottom surfaces before exiting the crystal 90. The angle of incidence is defined between the normal or perpendicular to the surface and the incident ray. It is noted that the size, shape and number of reflective surfaces is not limited to this example, and that crystals or transparent bodies having different numbers of surfaces and different sizes may be used.

In one embodiment, the polygonal shape formed by the reflective surfaces 92 has an uneven number of sides. Rays entering the crystal can move in the beam path 96, and propagate around the crystal a number of times based on the number of reflective surfaces 92.

The number of reflective surfaces 92 or sides n affects the maximum number of reflections $r_n$ that occur for a beam between entering and exiting the crystal, with the assumption that the exit and entry areas are on same surface (bottom or top) and do not overlap each other. For example, for an uneven number of sides, the maximum number of reflections can be represented by:

$r_n=4*n-1$ with $n=3,5,7,$

In contrast, for an even number of side areas, the number of reflections is:

$r_n=2*n-1$ with $n=4,6,8,$

On the way through the crystal, the beam hits several surfaces on which total internal reflection occurs. For a shape that corresponds to a regular polygonal prism, the angle of incidence of the beam (assuming a parallel beam) is the same for each area. To ensure that only total reflections occur on which no light enter or exit the crystal, the angle of incidence is greater than the critical angle of total internal reflection.

In order to transmit interrogation signals into the crystal and control the angle of incidence, an optical assembly (e.g., the optical assembly 62) is coupled to the entry area. An entry optical assembly includes one or more optical elements, such as lenses, collimators, waveguides, optical fibers, prisms and others. The optical elements may be connected to an optical fiber or fibers to a light source or coupled directly to the light source. An exit optical assembly including one or more optical elements may be coupled to the output area to guide the reflected beam to one or more detectors.

In one embodiment, the entry and/or exit optical assemblies include a coupling element to optically couple the light beam into and out of the crystal. For example, an optically transparent material is glued or otherwise bonded to the entry and/or exit area to prevent total reflection from occurring at the entrance and/or exit. In another example, the entry and/or exit area is whetted, ground or otherwise shaped so that the angle of incidence of the beam on the entry and/or exit area is less than the critical angle of total reflection. In another example, a portion of the crystal at the entry and/or exit area includes a material or is modified to provide an artificial layer that guides the beam through the first reflection.

The location and size of the entry and exit areas are not limited to the embodiments described herein. For example, the entry and exit areas can have any size and shape, e.g., based on the shape of an interrogation beam. In addition, the location of the entry and exit areas can be adjusted. The angle of incidence of the interrogation beam and/or the angle of the entry beam relative to the top and/or bottom surface can be controlled or adjusted to maintain the beam path within a selected portion of the crystal and maintain the angles of incidence larger than the critical angle.

For example, the entry and exit areas can be located to provide for space to accommodate an O-ring or other sealing mechanism, or to facilitate assembly of the crystal with a measurement apparatus. For example, as shown in FIG. 6, the entry and exit areas are located closer to the center of the crystal, as compared with the entry and exit areas shown in FIG. 5.

In the example shown in FIG. 6, moving the entry and exit areas closer to the center causes an oval ray path. The coupling assemblies are configured in this example to transmit the beam at a selected direction to ensure that the beam is incident on the reflective surfaces. This change in the path does not have any impact in functionality but has an advantage that there is more space between the entrance/exit areas and the borders of the crystal.

One or more surfaces of the crystal may be connected, attached or bonded to another structure. Such structures may be provided for mechanical stability (e.g., taking the forces of environmental pressure) and/or to attach the crystal to a measurement device. For example, as shown in FIG. 2, the crystal 52 is attached to a support structure 102 that is provided to allow the crystal 52 to be connected to the sample chamber 56 and held in place.

In one embodiment, a reflective coating or other means is provided so that an interrogation beam is reflected from the surface in contact with another structure (e.g., a supporting and/or sealing structure, an O-ring, etc.). This ensures that the beam does not enter or exit the crystal except for the input and exit areas.

Figure 7:
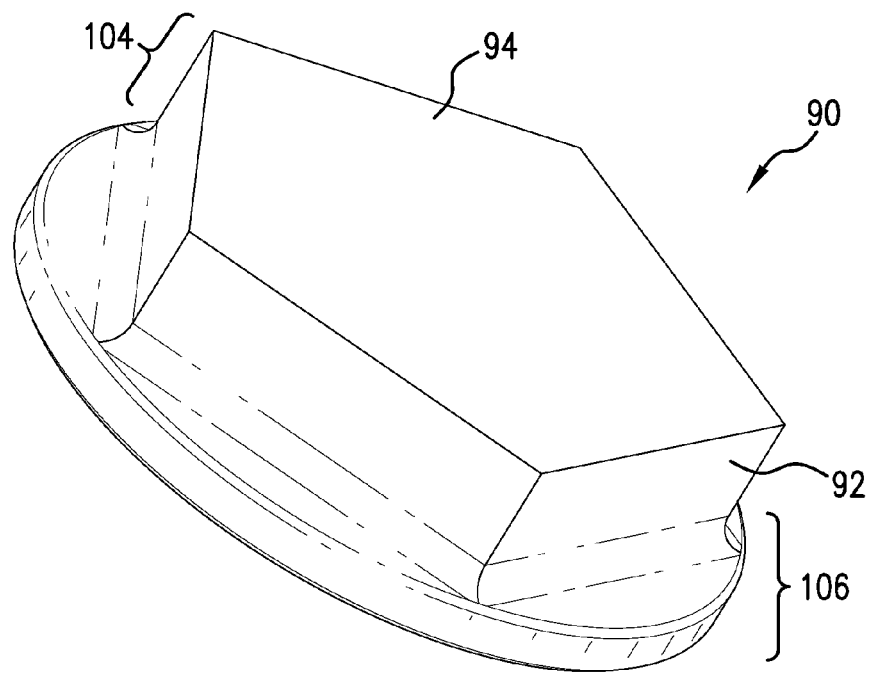
FIG. 7 is a perspective view of an embodiment of an internal reflectance solid transparent body.

In some instances, the crystal includes portions that are not intended or used for reflections. For example, as shown in FIG. 7, the crystal includes an upper portion 104 shaped as a polygon in which an interrogation beam propagates. The crystal also includes a lower portion 106 having a different shape. The lower portion 106 can have any shape or size, for example, to improve mechanical strength or facilitate attaching the crystal to other components. For example, the lower portion has a cylindrical shape, which would facilitate coupling the crystal to a chamber and sealing the crystal via an O-ring. The entry angle of the interrogation beam relative to the top or bottom surface can be adjusted to control the beam path and maintain the beam within the upper portion 104.

Figure 8:
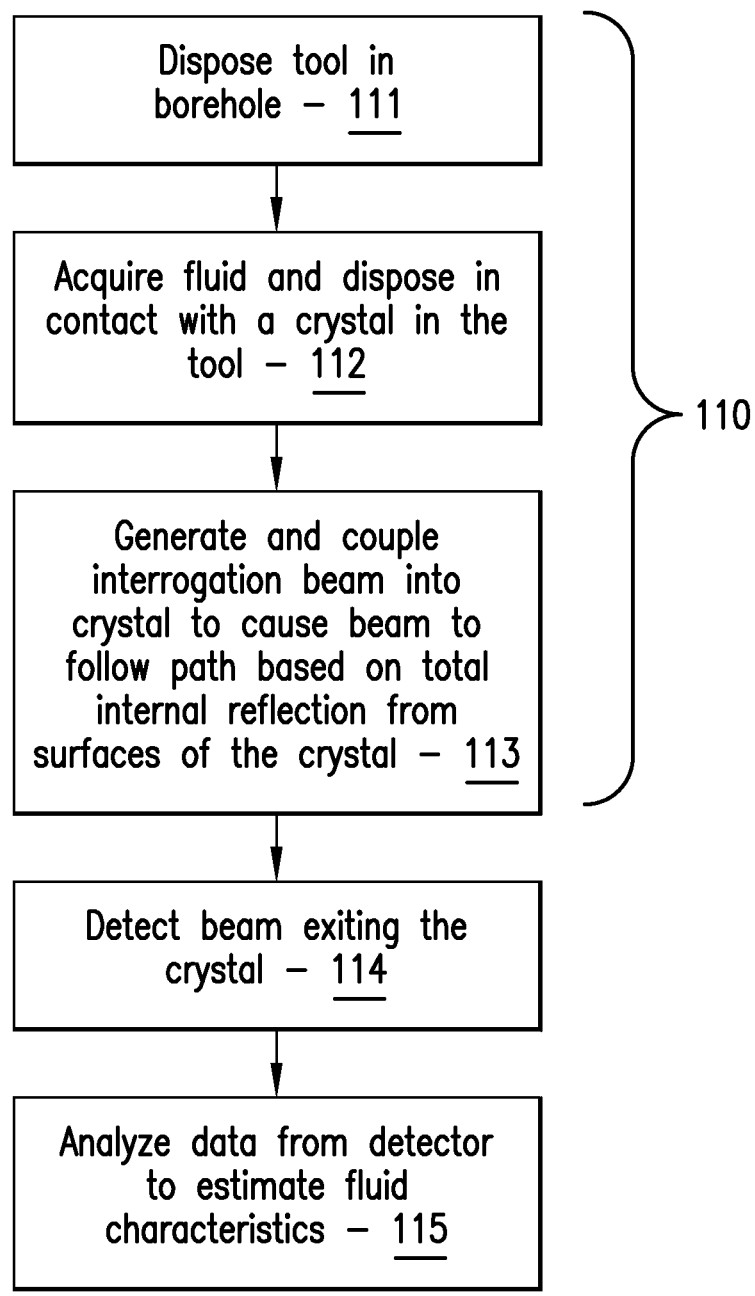
FIG. 8 is a flow chart illustrating an embodiment of a method of measuring characteristics of a material.

Referring to FIG. 8, an exemplary method 110 for measuring material parameters or characteristics is shown. The method 110 includes one or more stages 111-115. In one embodiment, the method 110 includes the execution of all of stages 111-115 in the order described. However, certain stages may be omitted, stages may be added, or the order of the stages changed.

In the first stage 111, an ATR spectroscopy tool such as the tool 18 is disposed in a borehole. In the second stage 112, a sample of formation fluid or other material is acquired and brought into contact with an internal reflectance crystal in the tool 18, such as the crystal 90. In the third stage 113, a light beam is transmitted into the crystal. For example, the light beam is transmitted into the crystal 90 in a direction such that light beam is internally reflected by the surfaces 92 in a circular or nearly circular path. In the fourth stage 114, the beam exits the crystal and is directed to a detector. In the fifth stage 115, data from the detected beam is analyzed to estimate characteristics of the fluid. For example, the processor estimates an amount of methane or other hydrocarbons based the intensity of received light at various frequencies. It is noted that the method 110 can be repeated for multiple light wavelengths to obtain absorption characteristics of the material for multiple frequencies or a frequency spectrum.

The apparatuses and methods described herein have various advantages over prior art apparatuses and techniques. The crystal has numerous advantages over prior art systems. For example, a common ATR crystal shape is an elongated (e.g., bar shaped) crystal that has an elongated reflective surface contacting a fluid to cause multiple reflections. In order to increase the number of reflections, the length of the crystal is increased, which is a disadvantage in that increasing the length can render the crystal too long for use in a downhole tool or cause the crystal to becomes mechanically unstable under downhole conditions (e.g. vibration and shock). The crystals described herein and accompanying spectrometry methods and apparatuses address such disadvantages.

In connection with the teachings herein, various analyses and/or analytical components may be used, including digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention.

What is claimed is:

1. An apparatus for measuring fluid characteristics, comprising:
a solid transparent body including a plurality of internally reflective surfaces configured to contact a material of interest and configured to internally reflect an electromagnetic radiation beam, the plurality of reflective surfaces defining a n-sided base surface having a polygonal shape and having at least three sides, each reflective surface forming a side of the polygonal shape, the base surface being at least partially perpendicular to the plurality of reflective surfaces, the body including an opposite surface having the polygonal shape and being at least partially perpendicular to the plurality of reflective surfaces, the body including an entry area configured to guide the electromagnetic beam into the body and toward the plurality of surfaces, the body configured to direct the electromagnetic radiation beam along a path within the solid transparent body from the entry area to an exit area on the solid transparent body, the body and the entry area configured to cause the electromagnetic beam to undergo only a selected number of reflections from the reflective surfaces until the electromagnetic beam exits the body via the exit area, wherein the selected number of reflections is less than or equal to a maximum number of reflections, the maximum number of reflections based on a position of the entry area, a position of the exit area and a number "n" of the sides;
an electromagnetic radiation source coupled to the entry area on the solid transparent body and configured to transmit the electromagnetic radiation beam into the solid transparent body through the entry area; and
a detector coupled to the exit area on the solid transparent body and configured to receive at least a fraction of the reflected electromagnetic radiation beam, the detector configured to generate a signal based on the received electromagnetic radiation beam and transmit the signal to a processor for at least one of analysis of material characteristics and data storage.

2. The apparatus of claim 1, wherein each of the plurality of reflective surfaces are side surfaces of the solid transparent body, each side surface has the same area, and each side surface has substantially the same angle between the side surface and adjoining side surfaces.

3. The apparatus of claim 1, wherein the solid transparent body includes at least one of a top surface and a bottom surface, wherein at least one of the top and the bottom surface is perpendicular to the plurality of reflective surfaces.

4. The apparatus of claim 3, wherein the material of interest is a fluid, the top surface is configured to be coupled to an electromagnetic radiation source, the bottom surface is configured to be submerged in the fluid, and both the entry area and the exit area are disposed at the top surface so that the entry area does not overlap the exit area.

5. The apparatus of claim 3, further comprising:
a support structure attached to at least one of the top surface and the bottom surface;
a reflective layer disposed on the at least one of the top surface and the bottom surface that is coupled to the support structure, the reflective layer disposed between the solid transparent body and the support structure, the reflective layer configured to totally reflect the electromagnetic radiation beam.

6. The apparatus of claim 1, further comprising an optical assembly configured to transmit the electromagnetic radiation beam in a direction that causes the electromagnetic radiation beam to reflect from each of the reflective surfaces and follow a finite chain of straight line segments in the solid transparent body from the entry area to the exit area.

7. The apparatus of claim 1, wherein the polygonal shape forms a regular polygon having an uneven number of equal length straight sides, each side forming the same angle with respect to an adjacent side.

8. The apparatus of claim 1, wherein the material is at least one of a subterranean formation fluid and a borehole fluid injected into a borehole.

9. The apparatus of claim 1, wherein at least the internal reflectance solid transparent body is disposed at a carrier configured to be disposed in a borehole in an earth formation, the material of interest is a borehole fluid, the apparatus further including a support structure in the carrier, the support structure configured to at least partially submerge the plurality of reflective surfaces in the fluid, submerge one of the base surface and the opposite surface in the fluid, and couple the entry area to an electromagnetic source at another of the base surface and the opposite surface.

10. A method of measuring fluid characteristics, comprising:
generating an electromagnetic radiation beam by a source coupled to an entry area on an internal reflectance solid transparent body including a plurality of reflective surfaces defining a n-sided base surface having a polygonal shape and having at least three sides, each reflective surface forming a side of the polygonal shape, the base surface being at least partially perpendicular to the plurality of reflective surfaces, the body further including an opposite surface having the polygonal shape and being at least partially perpendicular to the plurality of reflective surfaces;
transmitting the electromagnetic radiation beam into the solid transparent body through the entry area, the entry area located on one of the base surface and the opposite surface the body including an entry area configured to guide the electromagnetic beam into the body and toward the plurality of reflective surfaces;
guiding the electromagnetic radiation beam along a selected path through the solid transparent body to an exit area on the solid transparent body, wherein guiding includes totally internally reflecting the electromagnetic radiation beam from each of a plurality of internally reflective surfaces of the solid transparent body in contact with a material of interest, the body and the entry area configured to cause the electromagnetic beam to undergo only a selected number of reflections from the reflective surfaces until the electromagnetic beam exits the body via the exit area, wherein the selected number of reflections is less than or equal to a maximum number of reflections, the maximum number of reflections based on a position of the entry area, a position of the exit area and a number "n" of the sides;
receiving the electromagnetic radiation beam from the exit area at a detector; and
analyzing characteristics of the material of interest based on the received electromagnetic radiation beam.

11. The method of claim 10, wherein each of the plurality of reflective surfaces are side surfaces of the solid transparent body, each side surface has the same area, and each side surface has substantially the same angle between the side surface and adjoining side surfaces.

12. The method of claim 10, wherein the solid transparent body is an internal reflectance crystal.

13. The method of claim 12, wherein the solid transparent body includes at least one of a top surface and a bottom surface, wherein at least one of the top and the bottom surface is perpendicular to the plurality of reflective surfaces.

14. The method of claim 13, wherein the material of interest is a fluid, the bottom surface is configured to be submerged in the fluid, and both the entry area and the exit area are disposed at the top surface so that the entry area does not overlap the exit area.

15. The method of claim 13, wherein the solid transparent body is attached to at least one of the top surface and the bottom surface, and guiding the electromagnetic radiation beam includes internally reflecting the electromagnetic radiation beam by a reflective layer disposed on the at least one of the top surface and the bottom surface and disposed between the solid transparent body and the support structure.

16. The method of claim 10, wherein transmitting the electromagnetic radiation beam into the crystal includes transmitting the electromagnetic radiation beam in a direction through the entry area that causes the electromagnetic radiation beam to reflect from each of the reflective surfaces and follow a finite chain of straight line segments in the solid transparent body from the entry area to the exit area.

17. The method of claim 10, wherein the material is selected from at least one of a subterranean formation fluid and a borehole fluid injected into a borehole.

18. The method of claim 10, wherein at least the internal reflectance solid transparent body is disposed at a carrier configured to be disposed in a borehole in an earth formation, the material of interest is a borehole fluid, and the method includes at least partially submerging the plurality of reflective surfaces in the fluid and submerging one of the base surface and the opposite surface in the fluid during transmitting, guiding and receiving the electromagnetic radiation beam.

19. An apparatus for measuring fluid characteristics, comprising:
a solid transparent body including a plurality of internally reflective surfaces configured to contact a material of interest and configured to internally reflect an electromagnetic radiation beam, the plurality of reflective surfaces defining a n-sided base having a polygonal shape and having at least three sides, each reflective surface forming a side of the polygonal shape, the plurality of surfaces configured to direct the electromagnetic radiation beam along a path within the solid transparent body from an entry area to an exit area on the solid transparent body, wherein the solid transparent body includes at least one of a top surface and a bottom surface, wherein at least one of the top and the bottom surface is perpendicular to the plurality of reflective surfaces;
an electromagnetic radiation source coupled to the entry area on the solid transparent body and configured to transmit the electromagnetic radiation beam into the solid transparent body through the entry area;

a detector coupled to the exit area on the solid transparent body and configured to receive at least a fraction of the reflected electromagnetic radiation beam, the detector configured to generate a signal based on the received electromagnetic radiation beam and transmit the signal to a processor for at least one of analysis of material characteristics and data storage;

a support structure attached to at least one of the top surface and the bottom surface;

a reflective layer disposed on the at least one of the top surface and the bottom surface that is coupled to the support structure, the reflective layer disposed between the solid transparent body and the support structure, the reflective layer configured to totally reflect the electromagnetic radiation beam.

* * * * *